US00PP24000P2

(12) United States Plant Patent
Saul

(10) Patent No.: US PP24,000 P2
(45) Date of Patent: Oct. 22, 2013

(54) ***ANTIRRHINUM* PLANT NAMED 'SNAP DADDY PINK'**

(50) Latin Name: *Antirrhinum majus*
Varietal Denomination: Snap Daddy Pink

(75) Inventor: Robert Saul, Atlanta, GA (US)

(73) Assignee: Itsaul Plants, LLC, Alpharetta, GA (US)

( * ) Notice: Subject to any disclaimer, the term of this patent is extended or adjusted under 35 U.S.C. 154(b) by 83 days.

(21) Appl. No.: 13/506,019

(22) Filed: Mar. 21, 2012

(51) Int. Cl.
*A01H 5/00* (2006.01)

(52) U.S. Cl.
USPC ..... Plt./322

(58) Field of Classification Search
USPC ..... Plt./322
See application file for complete search history.

*Primary Examiner* — Annette Para
(74) *Attorney, Agent, or Firm* — Penny J. Aguirre

(57) ABSTRACT

A new cultivar of *Antirrhinum*, 'Snap Daddy Pink', characterized by its variegated foliage with distinct cream-colored margins and grey-green centers, its new growth tips with yellow margins and yellow-green centers, its multiple branches, and its 20 to 30 pink flowers per stem.

2 Drawing Sheets

Botanical classification: *Antirrhinum majus.*
Cultivar designation: 'Snap Daddy Pink'.

CROSS REFERENCE TO A RELATED APPLICATION

This application is related to a U.S. Plant Patent Application filed for a plant derived from the same breeding program that is entitled *Antirrhinum* Plant Named 'Snap Daddy Yellow' (U.S. Plant Pat. No. 21,845).

BACKGROUND OF THE INVENTION

The present invention relates to a new and distinct cultivar of *Antirrhinum majus*, and will be referred to hereafter by its cultivar name, 'Snap Daddy Pink'. The new cultivar represents a new snapdragon, a half-hardy perennial grown as an annual in containers and garden beds.

'Snap Daddy Pink' arose as a naturally occurring meristematic mutation of a plant that was growing in a container derived from seed of *Antirrhinum majus* seed strain Liberty Classic Mix (not patented) during bedding plant production at the Inventor's nursery in Alpharetta, Ga. 'Snap Daddy Pink' was selected as a single unique plant in November of 2010 after stable foliage variegation was obtained through multiple rounds of propagation by stem tip cuttings.

Asexual reproduction of the new cultivar was first accomplished by stem tip cuttings in November of 2010 in Alpharetta, Ga. under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar as grown in Alpharetta, Ga. These attributes in combination distinguish 'Snap Daddy Pink' from other varieties of *Antirrhinum* known to the Inventor.

1. 'Snap Daddy Pink' exhibits variegated foliage with distinct cream-colored margins and soft, grey-green centers.
2. 'Snap Daddy Pink' exhibits new growth tips with yellow margins and yellow-green centers.
3. 'Snap Daddy Pink' exhibits flowers that are pink in color.
4. 'Snap Daddy Pink' produces 20 to 30 flowers per stem (when grown in winter in a single poly greenhouse under natural light).
5. 'Snap Daddy Pink' is well branched.

The parent plant of 'Snap Daddy Pink', a seedling of the seed strain Liberty Classic Mix, differs from 'Snap Daddy Pink' in having non-variegated foliage that is dark green in color. 'Snap Daddy Pink' can be most closely compared to the cultivars 'Snap Daddy Yellow' and 'Eternal' (U.S. Plant Pat. No. 21,915), 'Peppermint' (unpatented) and 'Candy Stripe' (not patented), which are all similar to 'Snap Daddy Pink' in having variegated foliage. 'Snap Daddy Yellow' differs from 'Snap Daddy Pink' in having yellow flowers and new growth tips that are less yellow in color. 'Eternal' differs from 'Snap Daddy Pink' in being taller in height and less branched and in having flowers that are deeper pink in color. 'Peppermint' differs from 'Snap Daddy Pink' in having leaf margins that are less defined and in having a less vigorous growth habit. 'Candy Stripe' differs from 'Snap Daddy Pink' in having rose pink colored flowers and variegated margins that are wider and more variable.

BRIEF DESCRIPTION OF THE DRAWING

The accompanying colored photographs illustrate the overall appearance and distinct characteristics of the new *Antirrhinnum*. The photographs were taken of plants about 4 months in age as grown in a greenhouse in one-gallon containers in Alpharetta, Ga.

The photographs in FIG. 1 and FIG. 2 provide a view of the multiple branching, the foliage, and flowers of 'Snap Daddy Pink'. The colors in the photographs may differ slightly from the color values cited in the detailed botanical description, which accurately describe the colors of the new *Antirrhinum*.

DETAILED BOTANICAL DESCRIPTION OF THE PLANT

Figure 1:
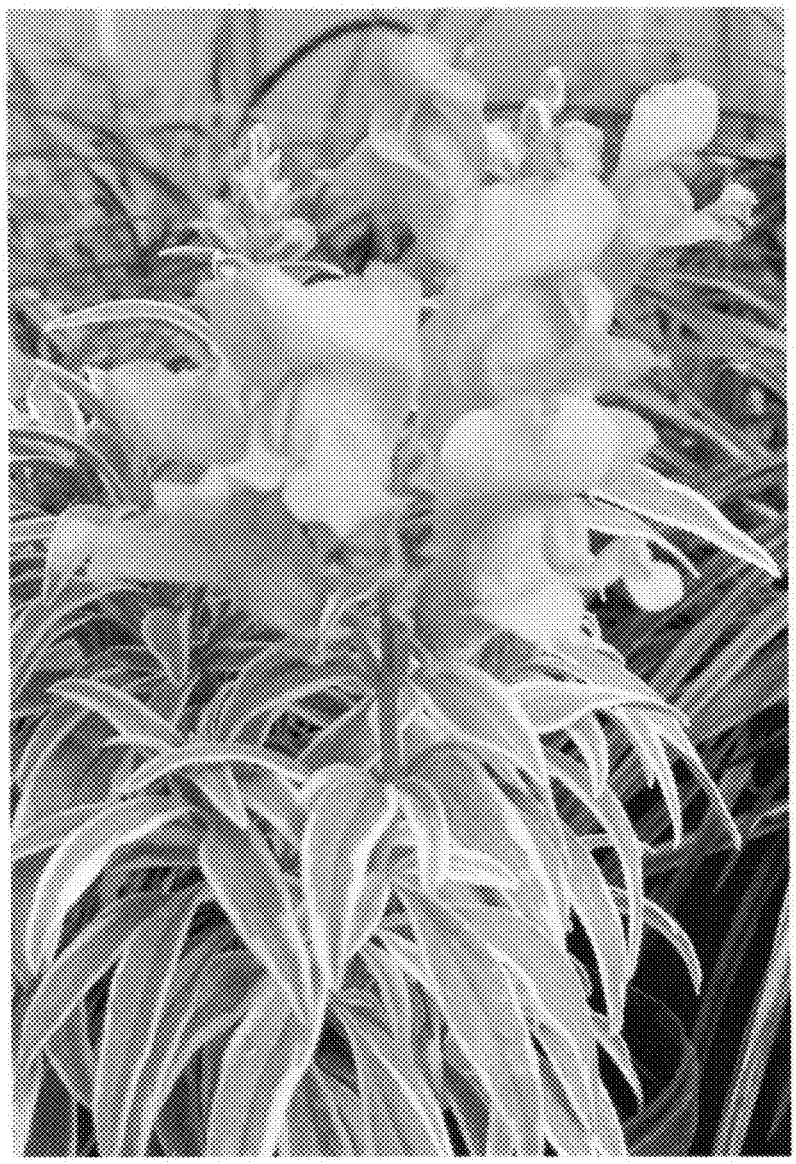
Figure 2:
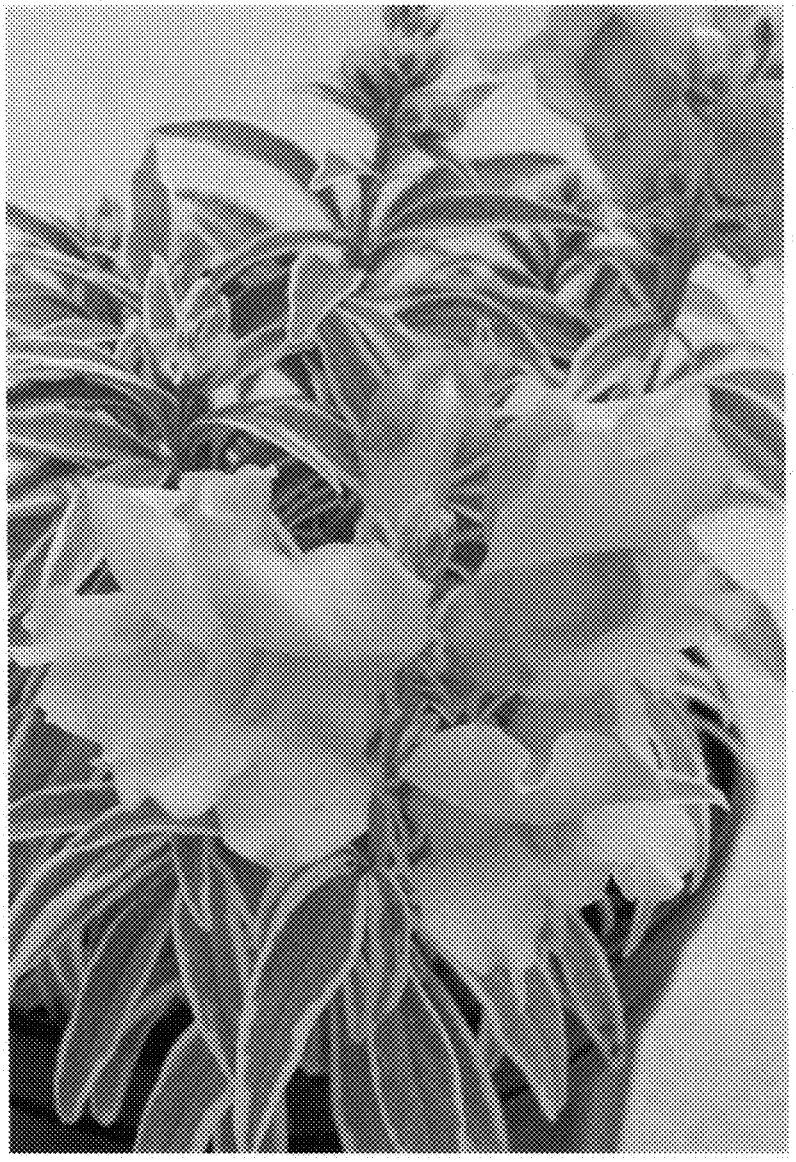

The following is a detailed description of plants about 4 months in age as grown in a greenhouse in one-gallon containers in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—March through November in Atlanta, Ga.

*Plant type*.—Half-hardy herbaceous perennial typically grown as an annual.

*Plant habit*.—Upright, dense.

*Height and spread*.—Reaches 30 to 38 cm in height and 20 to 25 cm in width.

*Cold hardiness*.—U.S.D.A. Zone 7.

*Diseases and pests*.—No susceptibility to diseases or pests has been observed.

*Root description*.—Fibrous.

Growth and propagation:

*Propagation*.—Stem cuttings.

*Root initiation and development*.—Roots initiate in about 2 weeks under mist and ambient light at 70° to 75° F., fully develop a 1.5 inch plug in 4 to 6 weeks, and finish in a 3.5 inch pot from a 1.5 inch plug in about 6 weeks.

*Growth rate*.—Moderate to vigorous.

Stem description:

*Branch habit*.—Well branched, an average of 10 lateral branches per basal stem.

*Stem size*.—Main stem; average of 30 cm (including peduncle) in length and 5.5 mm in width lateral branches; average of 15 cm in length and 3 mm in width.

*Stem shape*.—Oval.

*Stem color*.—A blend of 144D and 139D.

*Stem surface*.—Puberulent.

*Stem aspect*.—Upright, strong, with lateral branches held from 45° to nearly upright.

*Internode length*.—Up to 7 mm, lateral branches emerge near base.

Foliage description:

*Leaf shape*.—Lanceolate.

*Leaf division*.—Simple.

*Leaf base*.—Attenuate.

*Leaf apex*.—Narrowly acute.

*Leaf size*.—An average of 8 cm in length and 1 cm in width.

*Leaf venation*.—Pinnate, midrib recessed on upper surface, color on upper surface matches leaf color, color on lower surface 191C.

*Leaf margins*.—Entire.

*Leaf attachment*.—Sessile.

*Leaf arrangement*.—Whorled.

*Leaf surface*.—Dull and very finely puberulent on upper and lower surface.

*Leaf variegation pattern*.—Distinct creamy white margins an average of 1.5 mm in width with grey-green centers.

*Leaf color*.—Newly emerged (growth tips) upper and lower surface; centers 144C, margins; 4B, maturing upper surface; centers 146B, margins 4C, maturing lower surface; centers 138B, margins 4C, fully mature upper surface; 189A and margins, fully mature lower surface; centers 191A, margins 4D.

*Leaf number*.—Dense, an average of 30 mature leaves per lateral branch 9 cm in length.

*Leaf aspect*.—Cascading downward from stem.

*Leaf internode length*.—An average of 5 mm between whorls.

Flower description:

*Inflorescence type*.—Terminal racemes of bilabiate, blooms from the base to the apex.

*Inflorescence size*.—Average of 12 cm in length and 8 cm in width.

*Lastingness of flower*.—About 5 days, not persistent.

*Flower size*.—About 4.5 cm in depth and about 3.7 cm in diameter.

*Flower fragrance*.—Faint.

*Flower number per inflorescence*.—20 to 30 per stem in the winter when grown in a single poly greenhouse under natural light.

*Peduncle*.—Oval in shape, up to 15 cm in length and an average of 4 mm in width, a blend of 144D and 139D in color, surface is finely puberulent, flower internode length is an average of 5 mm.

*Pedicel*.—About 7.5 mm in length, about 2 mm in width, oval in shape, color is a blend of 144D and 139D in color, surface is pubescent with glandular hairs, one leaf at base; up to 3.5 cm in length and 9 mm in width with similar characteristics to stem leaves.

*Flower buds*.—Kidney-shaped, about 2.7 cm in length and 1.3 cm in width, color of petal portion is a blend of 149D, 62B, and 62D, calyx portion same as open flowers.

*Flower type*.—Bilabiate, held at about a 45° angle to peduncle.

*Calyx*.—Campanulate, about 1 cm in length and 1.8 cm in diameter, persistent.

*Sepals*.—5, fused at base only, elliptic in shape, 4.5 mm in width and 7 mm in length broadly acute apex, margins entire, variegated with centers 138A in color and margins 158A in color, outer surface is highly pubescent with glandular hairs, inner surface is puberulent and satiny.

*Corolla features*.—Bilabiate and fused to tube, upper lip; comprised of 2 kidney-shaped lobes that are cup-like, each lobe is about 2 cm in width and 2 cm in length with rounded apex, lower lip; comprised of a 2 lobe banner and a raised center lobe with keel and crested interior, combined an average of 2.8 cm in width and 1.8 cm in depth, lower surface of both lips sparsely pubescent and upper surface is glabrous, margins of both lips are entire and slightly ruffled, tube is about 3 cm in length and 1.2 cm in width, color of outer and inner surface of upper and lower lip and outer surface of tube is a blend of 62A, 62B, 62C and 63C with the inner is surface of the lower lip is marked with 12B on keel, color of inner surface of tube color is a blend of 62Dm and 62D with the crested region that extends into tube 12B.

*Receptacle*.—Disk-shaped, gelatinous, 144A in color, about 2.5 mm in diameter and 1.5 mm in depth.

Reproductive organs:

*Gynoecium*.—1 Pistil, about 2 cm in length, style is NN155A in color and 1.7 cm in length and 1.2 mm in width, stigma expanded club-shape at terminus and about 145D in color, ovary is superior, oblong in shape, 145D in color, 3 mm in length and width.

*Androcoecium*.—4 stamens, not united, about 2.2 cm in length; filament is 2 cm in length, 1 mm in width and NN155A in color; anther is amorphously shaped, about 1.5 mm in length and 1 mm in width and 13B in color, pollen is abundant in quantity and 11A in color.

*Fruit and seed*.—Fruit; a capsule, oblong in shape with a long thin beak, an average of 1.5 cm in length (including beak 6 mm in length and 1 mm in width), color is a blend of N199D, 200A and 202B, seeds; round, spiky, about 1.2 mm in diameter, 200B in color.

It is claimed:

1. A new and distinct cultivar of *Antirrhinum* plant named 'Snap Daddy Pink' as herein illustrated and described.

* * * * *